(12) United States Patent  
Schwabe

(10) Patent No.: US 7,477,384 B2
(45) Date of Patent: *Jan. 13, 2009

(54) DEVICE AND METHOD FOR INVESTIGATING ANALYTES IN LIQUID SUSPENSION OR SOLUTION

(75) Inventor: Nikolai Franz Gregor Schwabe, Oxford (GB)

(73) Assignee: ProImmune Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/826,295

(22) Filed: Jul. 13, 2007

(65) Prior Publication Data

US 2007/0268489 A1 Nov. 22, 2007

Related U.S. Application Data

(63) Continuation of application No. 10/497,006, filed as application No. PCT/GB02/05557 on Dec. 9, 2002, now Pat. No. 7,245,379.

(30) Foreign Application Priority Data

Dec. 12, 2001 (GB) ................................. 0129688.8

(51) Int. Cl.
*G01B 11/00* (2006.01)
(52) U.S. Cl. ...................................... 356/338; 356/337
(58) Field of Classification Search ......... 356/335–343, 356/432–442, 300
See application file for complete search history.

(56) References Cited

U.S. PATENT DOCUMENTS 4,801,205 A 1/1989 Tatsuno 4,942,305 A 7/1990 Sommer (Continued)

FOREIGN PATENT DOCUMENTS

DE 10029946 12/2001

(Continued)

OTHER PUBLICATIONS

Huebner J et al: "Integrated Optical Measurement System for Fluorescence Spectroscopy in Microfluidic Channels", Review of Scientific Instruments, American Institute of Physics, New York, US, vol. 72, No. 1, Jan. 2001.

(Continued)

*Primary Examiner*—Gregory J. Toatley, Jr.
*Assistant Examiner*—Tri T Ton
(74) *Attorney, Agent, or Firm*—Ked & Associates, LLP

(57) ABSTRACT

An optical detection device is provided for analyzing analytes in a liquid suspension or solution that can detect and process a large number of wavelengths of incident and fluorescent light simultaneously, which is small in size and can be easily adapted to different investigation requirements. In one embodiment an optical detection device comprises a light supplying means (45), an analyte handling means, (78), a light directing means (19), and detection means, integrated on planar substrate devices (40), (20), and (30), (30'), respectively. A plurality of optical waveguides are integrated in the substrate devices to direct light emitted by the light supplying means (45) through the different sections of the optical detection device to the detection means. The analyte handling means (78) comprises an analyte channel (70) for the liquid flow of the analyte suspension or solution and an analyte sorting means (72) comprising several sorting channels (72').

20 Claims, 11 Drawing Sheets

U.S. PATENT DOCUMENTS

| | | | |
|---|---|---|---|
| 4,945,400 | A | 7/1990 | Blonder et al. |
| 5,073,024 | A | 12/1991 | Valette et al. |
| 5,250,186 | A | 10/1993 | Dollinger et al. |
| 5,269,937 | A | 12/1993 | Dollinger et al. |
| 5,726,751 | A | 3/1998 | Altendorf et al. |
| 5,933,233 | A | 8/1999 | Gunther |
| 6,144,795 | A | 11/2000 | Dawes et al. |
| 6,315,955 | B1 | 11/2001 | Klein |
| 6,511,615 | B1 | 1/2003 | Dawes et al. |
| 2002/0028434 | A1 | 3/2002 | Goix et al. |
| 2002/0064800 | A1 | 5/2002 | Sando et al. |

FOREIGN PATENT DOCUMENTS

| | | |
|---|---|---|
| EP | 0535861 | 2/1998 |
| FR | 2783919 | 3/2000 |
| GB | 2218511 | 11/1989 |
| JP | 55058820 | 5/1980 |
| JP | 61110033 | 5/1986 |
| JP | 61145928 | 7/1986 |
| JP | 2285830 | 11/1990 |
| JP | 9145928 | 6/1997 |
| JP | 11503236 | 3/1999 |
| JP | 11513486 | 11/1999 |
| JP | 2001337030 | 12/2001 |
| WO | WO 93/20430 | 10/1993 |
| WO | WO 97/01087 | 1/1997 |
| WO | WO 99/54714 | 10/1999 |
| WO | WO 01/98759 | 12/2001 |
| WO | WO 03/008937 | 1/2003 |

OTHER PUBLICATIONS

Sobek D et al: "A Microfabricated Flow Chamber for Optical Measurements in Fluids" Proceedings of the Workshop on Micro Electro Mechanical Systems (MEMS) for Lauderdale, Feb. 7-10, 1993, New York, IEEE, US, vol. Workshop 6, Feb. 7, 1993.

Hübner, J., et al., "Integrated optical measurement system for fluorescence spectroscopy in microfluidic channels," Review of Scientific Instruments, (Jan. 2001), 72:1:229-233.

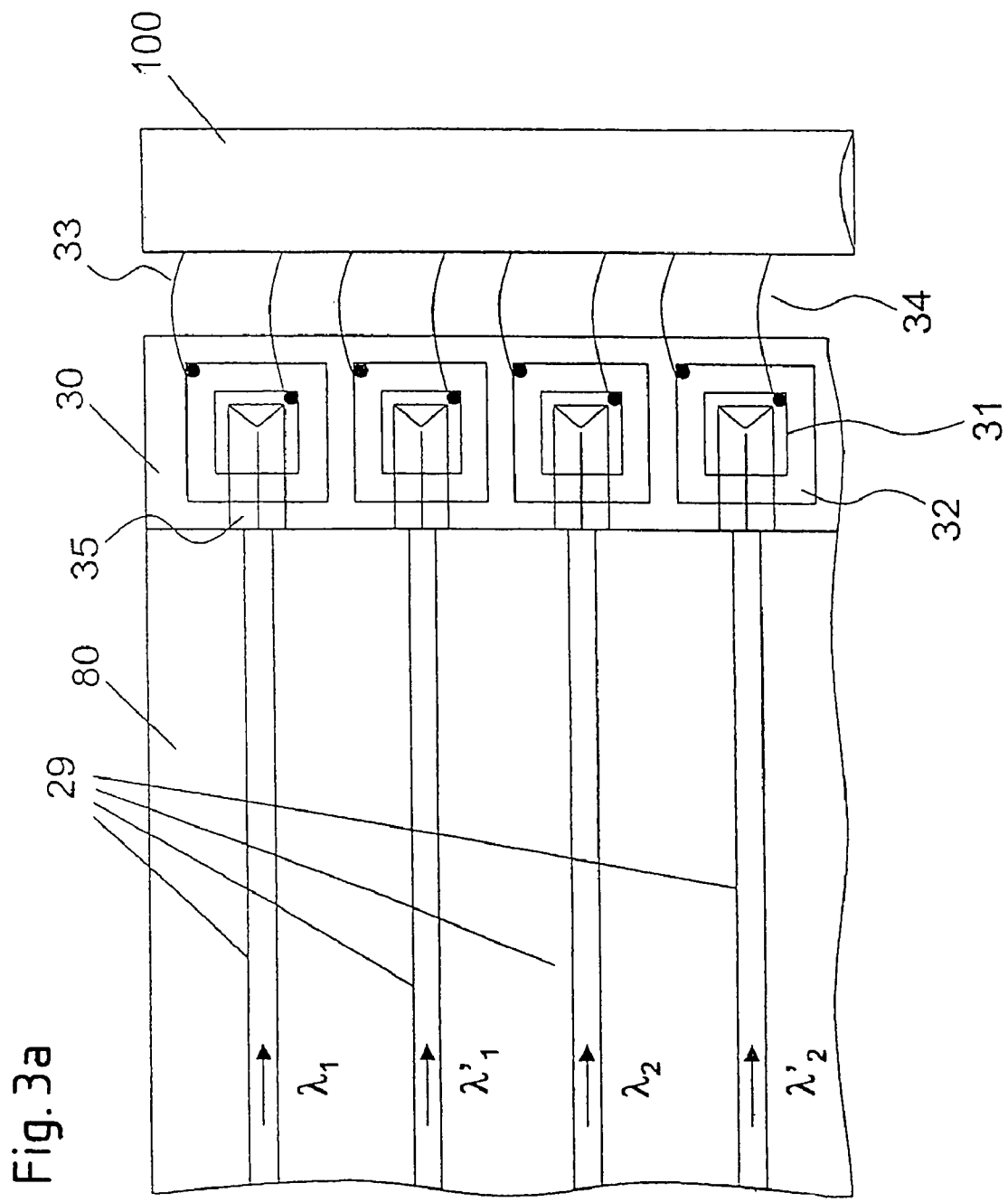

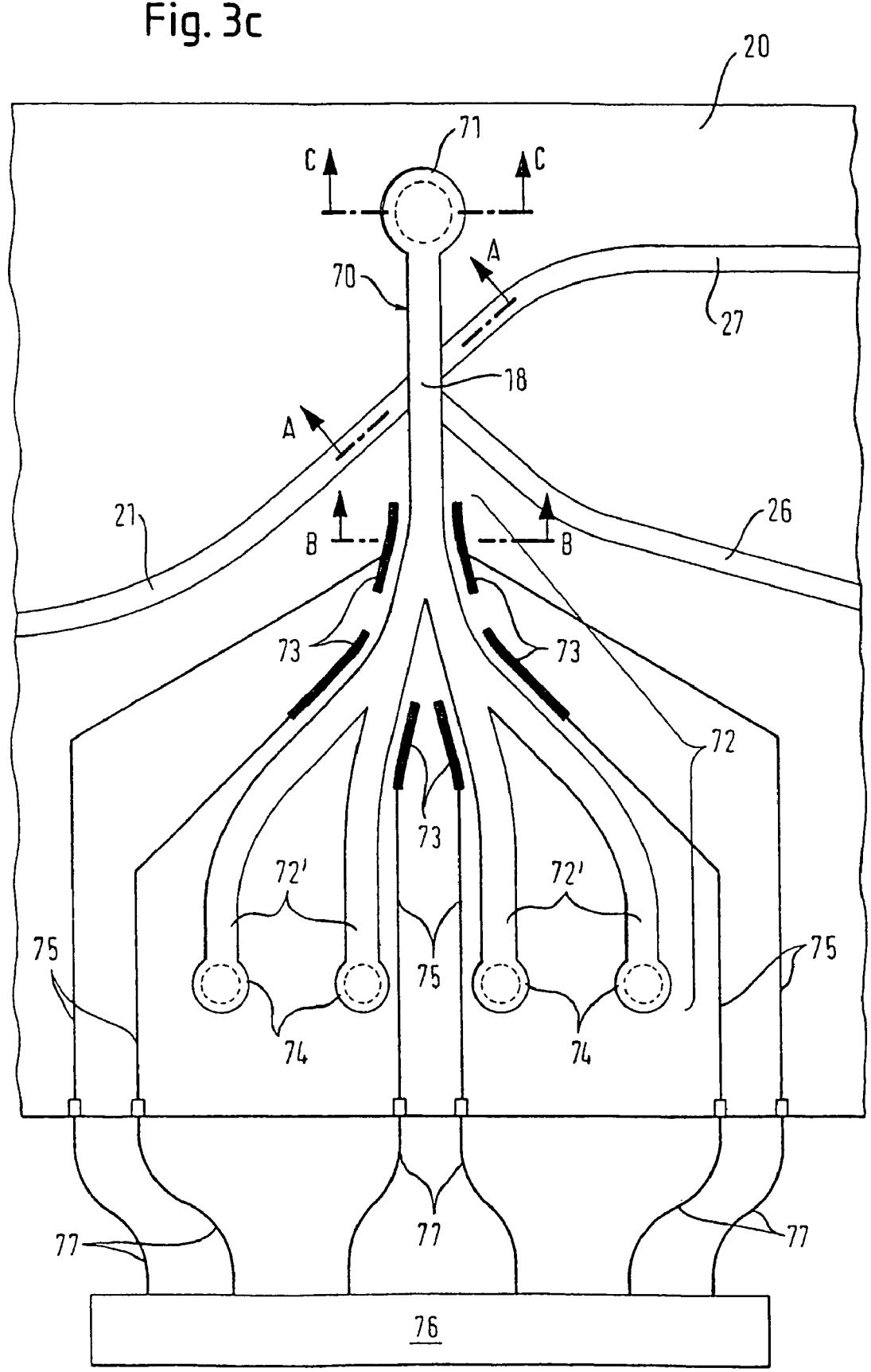

a)

b)

c)

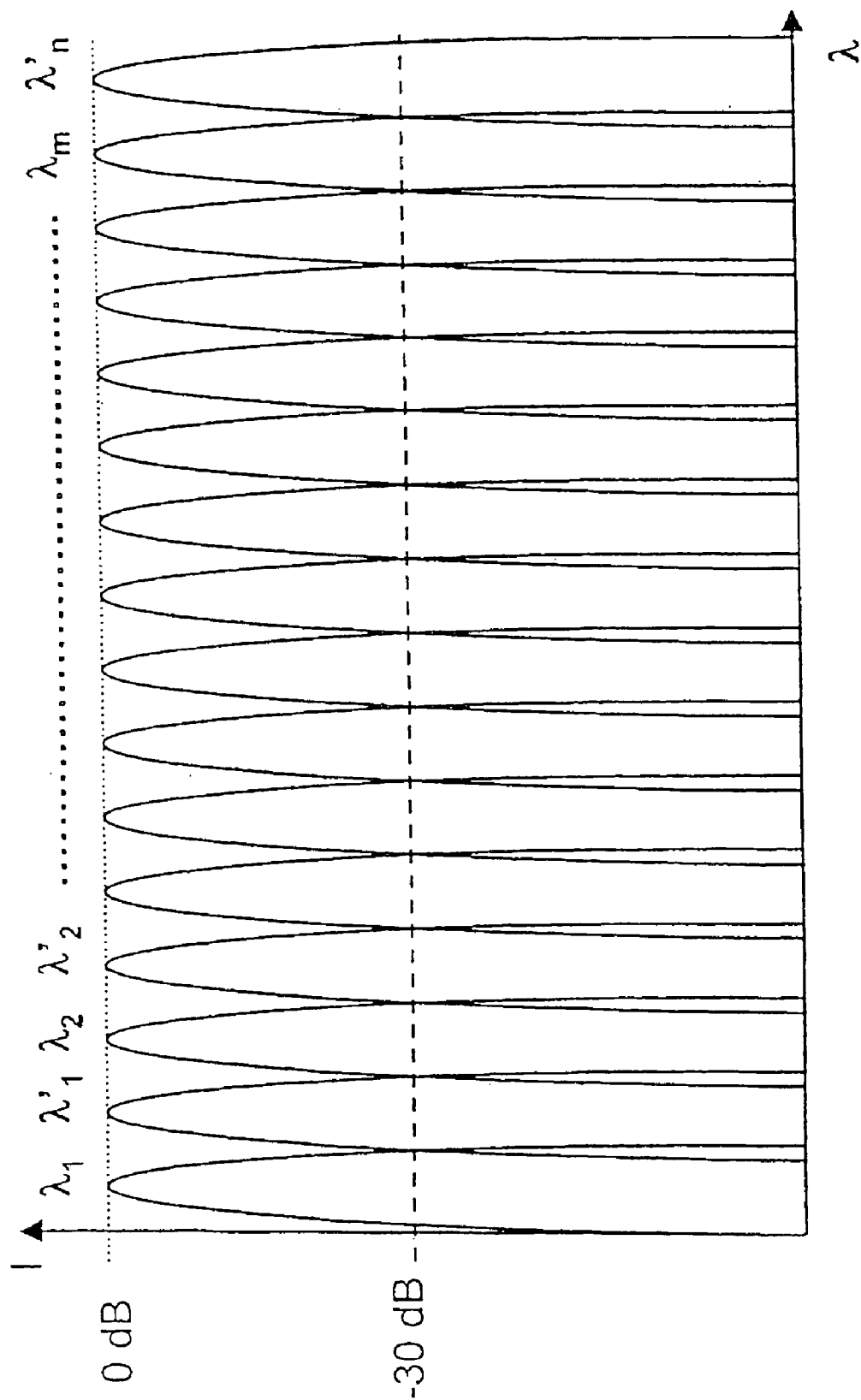

DEVICE AND METHOD FOR INVESTIGATING ANALYTES IN LIQUID SUSPENSION OR SOLUTION

This application is a Continuation of prior application Ser. No. 10/497,006, filed on May 27, 2004 (U.S. Pat. No. 7,245,379), that which claims priority to PCT/GB02/05557, filed Dec. 9, 2002, published on Jul. 3, 2003, Publication No. WO 03/054525 A2 in the English language and which claimed priority to GB 0129688.8, filed Dec. 12, 2001. The entire disclosure of the prior applications are considered as being part of the disclosure of the accompanying application and are hereby incorporated by reference therein.

FIELD OF THE INVENTION

The present invention relates to a device and a method for investigating analytes in liquid suspension or solution.

BACKGROUND OF THE INVENTION

Flow cytometry is a well-known fluorescent analysis technique, which can, for example, be used to detect and separate blood cells in a suspension according to their phenotypic properties. This can be achieved by staining the cells in the sample to be analysed for example with a monoclonal antibody specific to a phenotypic marker, which itself is coupled to a fluorescent dye. Different phenotypic cell surface markers can therefore be distinguished when dyes with different fluorescent wavelengths, e.g. green and red, are coupled to a number of different antibodies, each specific to a different marker.

To perform this analysis technique a Fluorescence Activated Cell Sorter, generally called FACS, is known, which is a complex device comprising optical and fluid-handling subsystems, which are usually assembled from discrete components. An example of such a FACS is disclosed in Roitt, Brostoff, Male, Immunology $5^{th}$ edition, Mosby Publishers (1998), p 385, and is shown in FIG. 1. In FIG. 1 a fluorescent-stained sample cell suspension 1 is introduced into a vibrating flow cell 2.

A cell flow 4 passing out of the flow cell 2 is encased in a sheath of buffer fluid 3, which has been separately introduced into the vibrating flow cell 2. The flow cell uses the principle of laminar flow and hydrodynamic focussing. A laminar flow of liquid, i.e. a flow that is non-turbulent, passing through a cylindrical tube will be subject to a viscous drag at the wall of the tube that leads to a higher flow velocity near the tube centre. The resulting velocity profile is that of a parabola. The so called Bernoulli effect associates such a differential velocity profile with a pressure gradient that points radially inwards from the tube wall, i.e. the pressure in the liquid flow decreases from the wall to the centre of the tube. This pressure gradient will move any particle in suspension in the flow into the centre of the flow where it will remain. To prevent blocking, a suspension of particles can be introduced into the tube through a wide bore which is surrounded concentrically by a larger bore containing sheath fluid. By constricting this coaxial flow whilst maintaining laminar flow a focused stream of particles can be obtained. If a suspension of discrete particles is introduced into the tube in this manner the particles will flow through the centre of the tube in sequence, aligned behind one another. The sheath fluid commonly used in flow cytometry is phosphate buffered saline solution or a similar electrolyte solution which can be charged electrically.

The flow 4 passing out of the flow cell 2 is illuminated by a laser 5 within an interrogation region. The emitted laser beam is scattered at the fluorescent-stained sample cells in the suspension in a characteristic manner according to the specific optical properties of the particles or analytes in the suspension and the fluorescent dyes used, to detect specific markers.

Scattered and fluorescent light passing from the cell flow and emerging from the interrogation region is collected by a light directing subsystem with a plurality of beam splitters 6, collimating and focussing lenses (not shown) and is directed to a detection subsystem with several detectors 7, 8, 9, 10. Detector 7 measures forward scatter of incident light from the laser, which allows for an estimation of the size of the cells in the flow 4 passing the laser 5. Similarly the granularity of cells can be detected, by collecting light scattered at a 90 degree angle with detector 8 after the light has been redirected by one of the beam splitters 6. Finally, detectors 9 and 10 detect, for example, red and green fluorescence, emitted by green and red fluorescent dyes, respectively, to identify surface markers present on the cells. This is achieved by collecting fluorescent light emitted in the same 90 degree path leading away from the flow 4 and by passing the light through a second beam splitter in the plurality of beam splitters 6 to illuminate the detectors 9 and 10. The detectors 9 and 10 are therefore designed to only detect light emitted in the green and red wavelength bands of interest, respectively.

Where possible, fluorescent dyes will be used that have a common excitation wavelength maximum that can be excited by a single light source and different emission wavelength maxima, such as in the green or red spectrum. Most commercial flow cytometry systems in use today will detect between 2 and 6 fluorescent wavelengths. The detectors themselves are in most cases photomultiplier tubes and the wavelength discrimination is normally achieved by inserting bandpass filters in the light path before the entry facet of the receiving tube. Because of the size of the individual components in the detection subsystem it is challenging to manage the spatial arrangement of all optical components when a system with a relatively large number of detectors is required. In such a situation, the lengths of different light paths from the flow cell to the respective detectors may vary substantially between different detectors. These constraints tend to limit the number of fluorescent wavelengths that are typically used in commercial applications today.

For the event that cell sorting may be required, the end of the flow cell 2 has a vibrating nozzle, which causes the flow 4 emanating from the flow cell into air to break up into droplets that usually contain no more than a single cell. These droplets, falling from the nozzle perpendicular towards the ground due to their initial velocity and gravity, enter into an analyte sorting subsystem, where they are subsequently passed through a charging collar 11, which applies a substantially uniform electrical charge to each droplet. When sorting is required, the data received by the detectors 7, 8, 9, 10 can be processed to steer electrostatic deflection plates 12 under computer control, which allows re-directing different cell populations in the flow 4 at different angles into different ones of a plurality of output sample tubes 13, according to the fluorescent and other optical properties detected.

In an alternative embodiment mechanical sorting is known wherein either the final receptacle collecting the flow emanating from the flow cell or its inlet is switched electromechanically in order to receive the relevant fraction of cells.

As mentioned before, typical commercial FACS devices in use today can distinguish between 2 and 6 fluorescent colours. At the same time they are bulky and expensive limiting their broad use in research and clinical practice. They require precision bulk optical and discrete mechanical components. At the same time, however, the requirement of researchers to distinguish a higher number of variables in analyte samples is increasing.

Cell sorters that detect a larger number of colours have been designed, but are not used in wide practice. This is mainly due to the fact that extending the existing bulk optical and fluidics technologies to higher numbers of colours that can be discriminated is very expensive and cumbersome.

There are also known first attempts of miniaturising FACS-devices. For example a conventional flow chamber of a FACS is replaced by microfluidic devices manufactured by micromachining technology like soft lithography. In a paper "A micorfabricated fluorescence-activated Cell Sorter" of Anne Y. Fu et al., Nature Biotech., Vol17, p. 1109 (November 1999) there is described a FACS for sorting various biological analytes. A cell sorting device is produced as a silicone chip with channels for a sample liquid. The chip is mounted on an inverted microscope, and fluorescence is excited near junctions of the channels with a focused laser beam generated by a bulk laser, which is directed onto the chip perpendicularly to the plane of the chip. The fluorescent emission is collected by the microscope and measured with a photomultiplier tube, which collects light emitted perpendicularly to the plane of the chip. The laser beam is focused perpendicular to the chip and a plurality of beam splitters, mirrors, etc. is necessary to guide the light.

U.S. Pat. No. 5,726,751 discloses a flow cytometer made of two components: a flow cytometer optical head and a disposable flow module. The flow module utilises a flow channel micromachined in a silicon wafer. The optical head comprises a laser to provide an illuminating beam and photodetectors. The laser and the photodetectors are arranged out of plane of the wafer, dependent on the angle of the analysing light beam, so that the photodetectors may collect the analysing beam.

SUMMARY OF THE INVENTION

It is an object of the present invention to provide an optical detection device for analysing analytes in a liquid suspension or solution that can be scaled to detect and process a large number of wavelengths of incident and fluorescent light simultaneously, which is small in size and can be easily adapted to different investigation requirements to enlarge the possibilities of its application.

According to a first aspect of the present invention, there is provided a device for analysing analytes in a liquid suspension or solution comprising, an analyte handling means including an analyte input region, an analyte channel for carrying analytes in a liquid suspension or solution comprising a light receiving region for receiving light from a light supplying means to illuminate the analytes in the interrogation region, an analyte output region, a light guiding means for directing light emerging from the analytes in an interrogation region of the analyte channel to an optical detection means for detecting one or more properties of the analytes in the suspension or solution, characterised in that at least the analyte channel and a first optical waveguide for guiding light emerging from the analytes in the analyte channel are integrated on the same first planar substrate.

Preferably, a second optical waveguide guiding light emerging from the analytes in the analyte channel is integrated on the first planar substrate.

Preferably, a third optical waveguide guiding light incident on the analytes in the analyte channel is integrated on the first planar substrate. L Preferably, the first optical waveguide is interfacing with the analyte channel, such that it collects light travelling in the analyte channel at an angle of between 30 and 60 degrees from the longitudinal axis of the analyte channel.

Preferably, the first optical waveguide is interfacing with the analyte channel, such that it collects light travelling in the analyte channel at an angle of substantially 45 degrees from the longitudinal axis of the analyte channel.

Preferably, the second optical waveguide is interfacing with the analyte channel, such that it collects light travelling in the analyte channel at an angle of between 60 to 120 degrees from the light collected by the first optical waveguide.

Preferably, the second optical waveguide is interfacing with the analyte channel, such that it collects light travelling in the analyte channel at an angle of substantially 90 degrees from the light collected by the first optical waveguide.

Preferably, doped absorbing regions may be provided on the first substrate adjacent to the analyte channel and the waveguide(s) for reducing the amount of unguided light propagating in the first substrate.

Preferably the refractive index of any or all of the waveguides substantially matches the refractive index of the analyte suspension or solution. Alternatively, or in addition, a single or multiple dielectric coating may be formed at the interface between the waveguides(s) and the analyte channel.

Preferably, the waveguide(s) may be tapered at their interface with the analyte channel.

According to another aspect of the invention, the third waveguide divides into two waveguides for injecting light into two spatially separate interrogation regions in the analyte channel and at least one waveguide is provided for collecting light emerging from the analytes adjacent to each one of the separate interrogation regions.

According to yet another aspect of the invention there is provided a method for investigating analytes in a liquid suspension or solution, particularly by using an optical detection device as described above.

According to yet another aspect of the present invention an analyte sorting means is provided for sorting different analytes with respect to their properties, which may have been detected by the optical detection device. The analyte sorting means includes an analyte channel with an analyte input for introducing the liquid suspension or solution of the analytes and a plurality of sorting channels comprising at least one y-junction in a staged cascade that is integrated on a substrate, wherein opposite polarity electrodes are formed in the substrate on either side of the at least one y-junction each for one investigated optical property of the analytes.

An analyte sorting means designed in this way enables the separation of analytes even of very small sample amounts.

In still another aspect of the invention, there is provided a light supplying means for use with a device for analysing analytes in a liquid suspension or solution, wherein one or several components of the light supplying means are integrated on a second planar substrate.

Preferably the light supplying means comprises at least one or more light emitting diodes or laser diodes are attached to the second planar substrate.

Preferably the light supplying means comprises at least one integrated optical waveguide for carrying light from the light emitting diode(s) or laserdiode(s) is leading from the light emitting diode(s) or laserdiode(s).

Preferably the light supplying means comprises several waveguides are leading from each one in an array of light emitting diodes or laserdiodes and a dispersive element is integrated on the second planar substrate for combining light of different wavelengths $\lambda_1 \ldots \lambda_m$ received from the waveguides into a single output waveguide.

Preferably the dispersive element is an arrayed waveguide grating or a transmission grating formed by an array of recesses etched into the second substrate.

In still another aspect of the present invention, there is provided a light directing means for use with a device for analysing analytes in a liquid suspension or solution, wherein at least one dispersive element, at least one optical waveguide for carrying light towards the dispersive element, and at least one plurality of output waveguides collecting light of wavelengths or wavelength bands $\lambda_1 \ldots \lambda_m, \lambda'_1 \ldots \lambda'_n$ to be separated by the at least one dispersive element are integrated on a third planar substrate.

Preferably the dispersive element(s) used in any of the light supplying and light directing means is/are (an) arrayed waveguide grating(s) or a transmission grating formed by an array of recesses etched into the second substrate.

Preferably, one dispersive element, one optical waveguide for carrying light towards the dispersive element, and one plurality of output waveguides collecting light of wavelengths or wavelength bands $\lambda_1 \ldots \lambda_m, \lambda'_1 \ldots \lambda_m$ to be separated are provided each for separating light received from a forward scatter path and for separating light from a side scatter path leading from an analyte interrogation region.

Preferably any of the first, second and third substrate is made of any of silica and silica-on-silicon and silicon-on-insulator.

In still another aspect of the present invention, there is provided a detection means for use with a device for analysing analytes in a liquid suspension or solution, wherein at least one optical detector is integrated in or hybridised on a fifth planar substrate.

Preferably, a plurality of optical detectors is provided with one detector each being provided for detecting a different one of the wavelengths $\lambda_1 \ldots \lambda_m, \lambda'_1 \ldots \lambda'_n$.

Preferably the detectors are photodiodes.

Preferably, each detector is mounted on top of one of several v-grooves terminating in an inclined end face formed in the fifth substrate, the v-grooves extending to the edge of the substrate.

Preferably, the fifth substrate is butt-coupled to the third substrate and bonded by means of an appropriate glue or resin.

Preferably, each in the plurality of detectors receives light from a different waveguide in at least one of the pluralities of output waveguides integrated in the third planar substrate.

In another aspect of the invention, an array of detectors is provided each for receiving light transmitted from a forward scatter path and light transmitted from a side scatter path leading from an analyte interrogation region.

In another aspect the invention provides for a device for analysing analytes in a liquid suspension or solution, including an analyte handling means, an analyte sorting means, a light supplying means, a light directing means, and the light detecting means as described herein.

In another preferred embodiment of the present invention, at least two of the analyte sorting means, the light supplying means, the light directing means, and the light detecting means are connected by optical fibres. Releasable connections between optical fibres leading from the respective means may be made by means of optical fibre connectors.

In yet another preferred embodiment of the present invention, at least two of the analyte sorting means, the light supplying means, the light directing means, and the light detecting means are integrated on the same planar substrate.

Another aspect of the invention concerns the use of the an optical detection device as described herein for investigating the properties of one or more analytes in a liquid suspension or solution.

Preferably, use of an optical detection device as described herein is made, wherein the optical properties of the one or more analytes in the suspension or solution are marked by markers with known optical properties and the one or more wavelength or wavelength band(s) $\lambda_1, \ldots, \lambda_m$ of the light supplying means are selected according to emission and absorbtion maxima of the used markers.

Preferably, the markers for the analytes are fluorescent.

Preferably, sorting of the analytes of the suspension or solution according their different optical properties is acheived by guiding them into different sorting channels according to the different properties detected.

In another aspect, the invention concerns a method for investigating analytes in a liquid suspension or solution using an optical detection device as described herein.

Preferably the method for investigating analytes in a liquid suspension or solution using an optical detection device as described herein is carried out, wherein at least two wavelengths or wavelength bands $\lambda_1, \ldots, \lambda_n, \lambda'_1, \ldots, \lambda'_n$ in the light emerging from the analytes are detected simultaneously.

The flow of the analyte suspension or solution through the analyte channel and the sorting channels may be reversible.

Manufacturing each of the different means of the optical detection device on separate semiconductor devices and connecting these devices by optical fibres, etc., substantial distances can be bridged. Therefore it is e.g. possible to arrange the analyte handling means in an experimental hood, use light supplying means, that is installed in a separate room, and set up the detection means in still a further room.

By designing a device for analysing analytes in a liquid suspension or solution according to the present invention a very compact and high channel count system can be realised cost-effectively. This allows saving valuable bench-space in laboratory or point-of-care applications, or even the realisation of a hand-held device. The optical detection device can be manufactured, to a large extent with high-volume semiconductor processing technologies like lithographic patterning, masking and etch processes or the like, which allow for the realisation of very high specification and narrow tolerance devices in high volumes and at low cost. The possibility of arranging the different sections of the optical detection device and the discrete components of these sections independently from one another on the substrates permits an assembly of the device, that can be optimised according to certain requirements, e.g. of the analytes, the light source or the components. The present invention will therefore enable use of a described flow-cytometric and similar industrial and/or biomedical analyte detection and handling applications in new areas of medical and scientific use.

By integrating the channel and the waveguides on the surface of a planar substrate the total amount of space required by the optical detection device can be reduced substantially.

Through using the components and processes described herein known components and techniques the device for analysing analytes can be manufactured very cost efficiently. Additional objects and advantages of the invention will be set forth in the detailed description which follows, and will be obvious from the description. Preferred or optional features of the invention will also be apparent from the appended claims.

BRIEF DESCRIPTION OF THE DRAWINGS

In order that the invention may be more readily understood embodiments will now be described, merely by way of example, with reference to the accompanying drawings in which:

FIG. 3a is a schematic enlarged top view of the detection means of the of the optical detection device of the present invention;

FIG. 3c is a schematic enlarged top view of the layout of the liquid channels and optical waveguides within the analyte handling means;

FIG. 6 is a schematic representation of the optical output spectrum of the optical detection device of the present invention.

DETAILED DESCRIPTION OF PREFERRED EMBODIMENTS OF THE INVENTION

Figure 1:
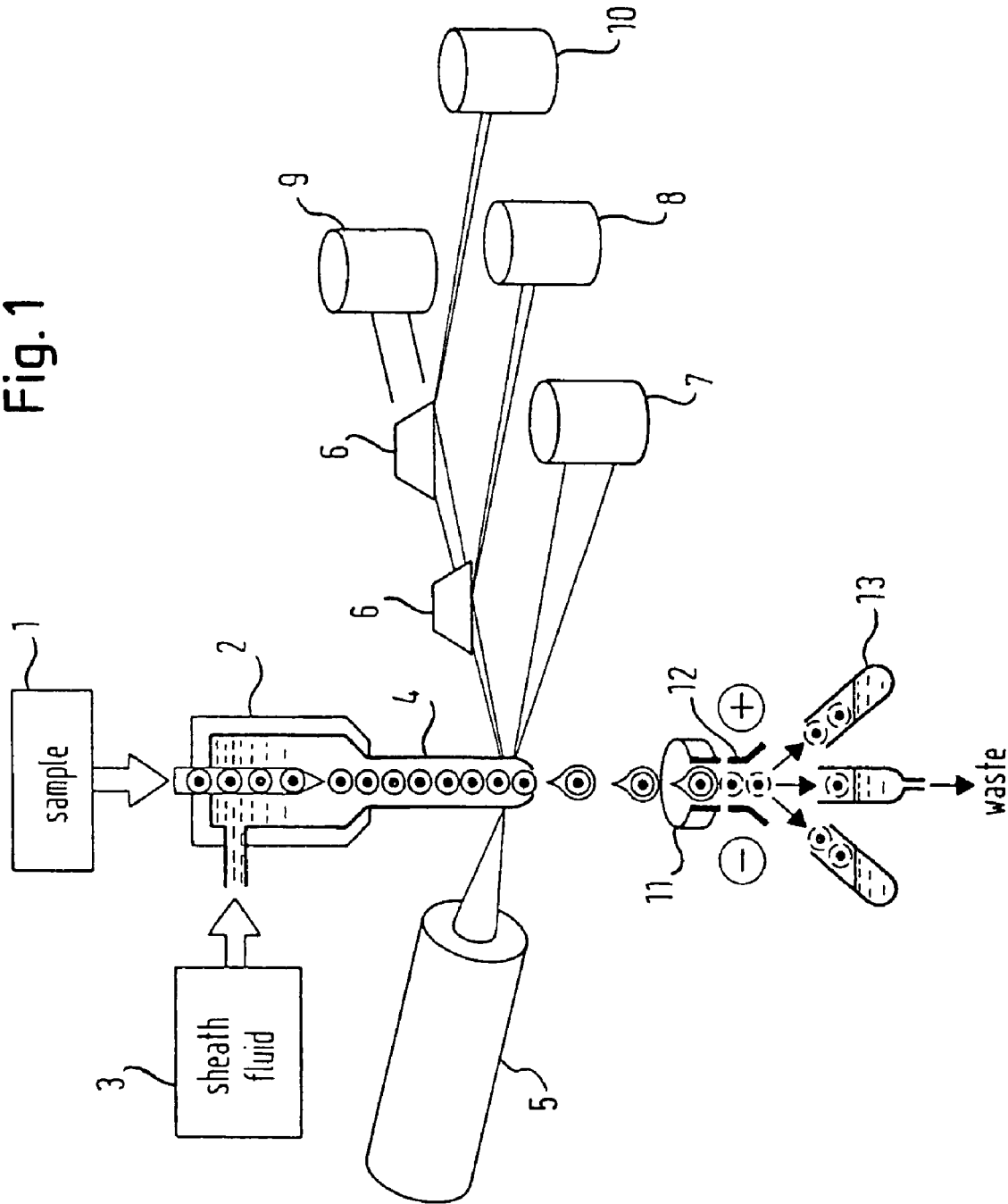
FIG. 1 is a schematic view of a known fluorescence activated cell sorter as known in the prior art.
Figure 2A:
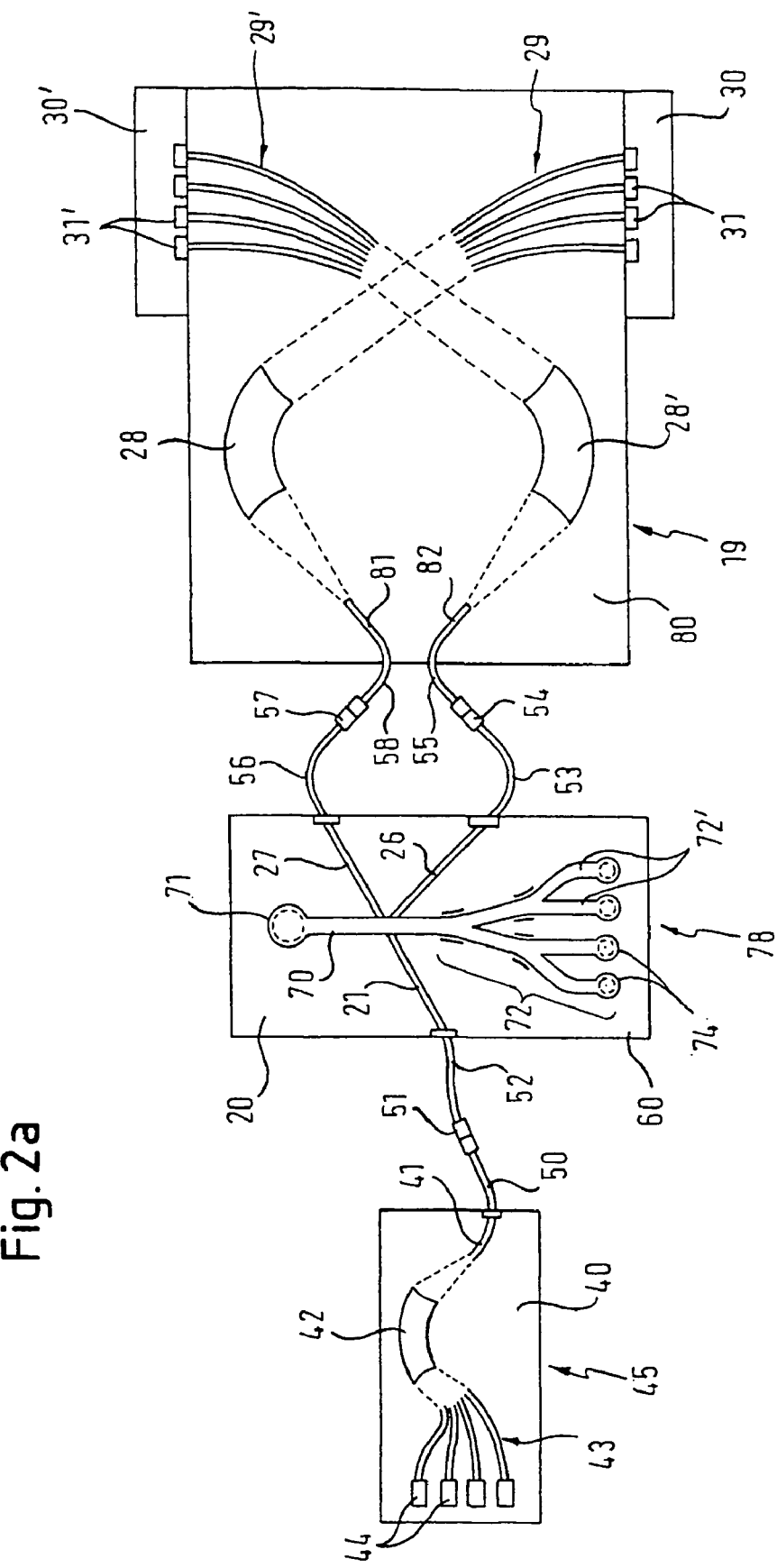
FIG. 2a is a schematic top view of an optical detection device according to one embodiment of the present invention.

In FIG. 2a an embodiment of an optical detection device according to the present invention is shown, which comprises a light supplying means 45 integrated on a planar substrate device 40, an analyte handling means 78 integrated on a planar substrate device 20, a light directing means 19 integrated on a planar substrate device 80, and detection means integrated on planar substrate devices 30, 30'. Also shown is a plurality of optical waveguides, which are integrated in the substrate devices and are designed to direct light emitted by the light supplying means 45 through the different sections of the optical detection device to the detection means. In the analyte handling means 78 there is shown an analyte channel 70 for the liquid flow of the analyte suspension or solution and an analyte sorting means 72 comprising several sorting channels 72' for different properties of the analytes.

The planar substrate devices 20, 40, 80 may for example be a silica or silica on silicon substrate and optical waveguides formed in the substrates may be buried channel waveguides formed by methods well known in the art of integrated optics, such as described in WO0125827. Alternatively the substrates 20, 40, 80 may be silicon-on-insulator and the waveguides formed as silicon-on-insulator ridge waveguides methods for forming integrated silicon on insulator ridge waveguides are described in WO9508787 and in a paper entitled "Low Loss Single Mode Optical Waveguides with Large Cross-Section in Silicon on Insulator" by J. Schmidtchen et al in Electronic Letters, 27, p. 1486, 1991. Further methods for manufacturing silicon-on-insulator optical waveguides are described in WO0036445, WO0025156. The planar substrate device 30 may be formed may be silicon.

The light supplying means 45 may be a discrete wavelength multiwavelength light source for emitting light with a predetermined characteristic, which is changeable by interaction of the light with analytes in suspension or solution according to the properties of the analytes. If the system is used for detecting fluorescence, a m-channel device may have a light source emitting m discrete wavelengths or narrow wavelength length bands $\lambda_1, \ldots, \lambda_m$ which are selected according to the properties of the analytes to be investigated. For example, $\lambda_1, \ldots, \lambda_m$ may be within a narrow tolerance of the absorption maxima of n selected fluorescent markers to be used in detection, which can be excited to fluoresce on fluorescent wavelengths or narrow wavelength bands $\lambda'_1, \ldots, \lambda'_n$. The fluorescent markers used may be known fluorescent chemical or biological molecules or fluorescent beads or particles that have characteristic fluorescent properties due to their chemical properties and or physical dimensions. Preferably none of the wavelengths or wavelength bands $\lambda_1, \ldots, \lambda_m$, $\lambda'_1, \ldots, \lambda'_n$ overlap to an extent where it would be difficult to distinguish the signals carried in them. In practice the overlap should be preferably less than −20 dB and more preferably less than −30 dB. If all absorption maxima of the n fluorescers are different in wavelength from one another m will be equal to n. However, in case some of these absorption maxima overlap m will be less than n.

Therefore there are provided m light emitters 44 generating light of wavelengths or wavelength bands $\lambda_1, \ldots, \lambda_m$. The light emitters 44 may be distributed feedback lasers (DFB lasers) or external cavity lasers, as described in WO0003461, that are integrated or hybridised on the substrate 40 in a linear array. Methods for hybridising an active light emitting element on a substrate in alignment with an output waveguide is described, for example in WO9743676. The active light emitting element in this assembly is typically formed from a combination of type II, III, V, VI semiconductor materials according to methods well known in the art. If an external cavity laser is chosen and the substrate material in which waveguides are formed is silica, then the grating forming the front reflector of the cavity may be provided by using methods similar to those well known in the art for forming optical gratings in telecommunications fibres. A waveguide 43 is leading from each of the light emitters 44 to a dispersive element 42 that is used to multiplex the light output from the various light emitters 44 into a single waveguide 41, which leads to the edge of the substrate 40 where it connects to the fibre 50.

If silicon-on-insulator is chosen for the substrate 20, 40, 80, then the optical analysis will have to be carried out at wavelengths greater than 1100 nm, as silicon is not transparent at wavelengths shorter than 1100 nm. This does not pose a problem, however, as optical components such as laser diodes and photodetectors are commonly available for such wavelength requirements. Fluorescent dyes or particles have to be used accordingly, which have both their absorption and emission maxima at wavelengths greater than 1100 nm.

Using a dispersive element 42 in the multiplexing process is well known in the art and has the advantage of minimising transmission losses. Examples of forming such dispersive elements can be found for example in U.S. Pat. No. 5,029,981, and U.S. Pat. No. 5,467,418, both of which describe arrayed waveguide type elements well known in the art of integrated optics. In these cases a plurality of unequal length waveguides (the waveguide array) causes the necessary phase difference in the light front travelling through the array to generate the desired dispersion. Another embodiment of a dispersive element is disclosed in EP 0365125, in which a one-dimensional reflective-type diffraction grating is formed in an slab waveguide by a one-dimensional array of wells formed with walls that are substantially perpendicular to the plane of the substrate 40.

The connection between the fibre 50 and the waveguide 41 can be carried out by means well known in the art, using methods such as described, for example, in WO 97042534, WO9835250, WO9839677, WO9957591, and WO0129598, and by other methods well known in the art. The fibre may be a multimode or more preferably a single mode silica fibre, such as commonly used in telecommunications applications. A typical single mode optical fibre will have a 125 micrometer silica cladding and a 8 micrometer single mode silica core whereby the silica in the core has a higher refractive index than the silica in the cladding.

The fibre 50 connects via a connector 51 to an input fibre 52 to the edge of the planar substrate device 20. The connector 51 may be a standard fibre-to-fibre connector, such as those commonly used for making connections between optical telecommunications fibres. On the substrate 20 an optical waveguide 21 collects the multiwavelength light beam received from the light supplying means 45 in the fibre 52. The connection of fibre 52 to waveguide 21 can be provided in the same manner as described above for the connection between fibre 50 and waveguide 41.

The waveguide 21 directs the light beam to the analyte channel 70 located on the planar substrate device 20. The liquid suspension or solution of the analytes is introduced into the analyte channel 70 via the input port 71 and flows through the channel 70 towards an analyte sorting means 72 (described in more detail later on), comprising a plurality of sorting channels 72' that each lead to one in a plurality of output ports 74. The analyte channel 70, the analyte sorting channels in the plurality 72', the input port 71, and the output ports in the plurality 74, are formed in the substrate 20 as an extended pattern of recesses that are formed by machining into the top surface of the substrate or patterned by standard lithographic processes and etched into the top surface of the substrate using processes well known in the art of semiconductor manufacturing, such as reactive ion etching.

Light is injected into an interrogation region 18 within the analyte channel 70 from the waveguide 21. If the waveguides are formed in a silica or a silica-on-silicon substrate, the waveguide 21 interfaces with the analyte channel 70 at an angle, such that light refracted across the interface of the analyte channel 70 with the waveguide 21 will enter the analyte suspension or solution carried in the channel at an angle of 30 to 60 degrees to the axis of the analyte channel, and more preferably at an angle of approximately 45 degrees. Analytes present in an analyte suspension are labelled with fluorescent dyes. As will be described in more detail later on the analyte suspension passes through the analyte cannel 70, travelling past the interrogation region 18 where the analytes are illuminated by the light received from the waveguide 21. The analytes in the suspension have been pre-stained, according to methods well known in the art of flow cytometry, with a range of n fluorescent dyes each specific to a given phenotypic property of the analytes to be detected, illuminating of the stained analytes by light injected into the interrogation region 18 from the waveguide 21 causes a combination of absorption, scattering and fluorescence in the analytes within the interrogation region 18.

Preferably the refractive index of the waveguide 21 and that of the analyte suspension or solution in the analyte channel 70 are matched in order to avoid significant reflection losses. Such index matching can be achieved, for example by varying the buffer formulation for the analyte suspension or by doping the optical waveguides used. In an embodiment where a residual mismatch between the analyte suspension or solution and the optical waveguides on the substrate 20 cannot be avoided, antireflective coatings may be formed on the sidewalls of the analyte channel 70 in the interrogation region 18 according to processes well known in the art of integrated optics to reduce backreflections at the interfaces further. In such an event the angle of refraction at such interfaces will also have to be taken into account according to the standard principles of wave optics, with the aim that light injected in the analyte suspension will travel at an angle of 30 to 60 degrees to the axis of the analyte channel 70, and more preferably at an angle of approximately 45 degrees. On the opposite side of the analyte channel 70 after the light has passed the interrogation region 18 forward-scattered light is collected by waveguide 27 and 90 degree scattered and fluorescent light is collected by waveguide 26. Consequently the waveguides 26 and 27 are arranged to collect light travelling at an angle of 0 and 90 degrees within the analyte suspension or solution, respectively, with respect to the angle of incident light travelling in the analyte suspension or solution. If there is no index mismatch between the suspension or solution and the waveguides, this translates to an angle between the waveguides 26 and 27 of 90 degrees, but in a situation where these refractive indexes are not matched, different angles between the waveguides 26 and 27 and between these waveguides and the side face of the analyte channel will have to be determined according to standard principles of wave optics. Usually the purpose of detecting forward scattered light is to determine the size of the analyte particles and the purpose of detecting 90 degree scattered light is to detect the granularity of these particles, as well as any fluorescence emitted by them. A particular advantage of this arrangement is that it is possible to collect fluorescent light at a higher signal to noise ratio than when it is collected in the forward scatter path. The waveguides 21, 26, 27 may conveniently be tapered at the interface with the analyte channel 70 to improve the optical transmission characteristics of their interfaces. The cross section of the waveguides 21, 26, 27 at the interface with the analyte channel 70 will preferably be in the region of 1 micron to 10 micron diameter and more preferably between 3 micron and 8 micron diameter. Preferably, the analyte channel 70 will have a cross section between 5 micron and 100 micron diameter and more preferably between 10 micron and 25 micron diameter.

The light emerging from the interrogation region 18 after interaction with the analytes in the liquid suspension or solution is guided by the waveguides 26 and 27 to the edge of the substrate 20 where they connect to optical fibres 53 and 56, respectively. Light transmitted to these fibres is transmitted via fibre optic connectors 54 and 57 to optical fibres 55 and 58, respectively, which transmit light guided in these fibres to the light directing means 19 integrated on the substrate 80. The optical fibres 53, 55, 56, 58 and connectors, 54, 57 are similar to those components described above for connecting the light supplying means 45 to the analyte handling means

78. Light received from the optical fibres 55 and 58 is collected by the waveguides 82 and 81. Light travelling in the waveguides 81 and 82 subsequently passes to the integrated dispersive elements 28, 28'. The dispersive elements 28, 28' are designed similarly to the dispersive element 42 on the light supplying means 45, preferably either as an arrayed waveguide grating or as a transmission or reflection grating described before. The purpose of the dispersive elements 28, 28' is to divide the light travelling in the waveguides 81, 82 into a number of discrete wavelength bands to be detected in the forward and side scatter path from the analyte handling means 78, respectively. Typically, the wavelengths to be detected will be the wavelengths $\lambda_1, \ldots \lambda_m$ emitted by the light supplying means 45 and the wavelengths $\lambda_1, \ldots, \lambda_n$ emitted by the fluorescent markers used. Normally m will be less or equal to n, and therefore the maximum number of wavelength bands to be detected will be less or equal to 2n. The m+n discrete wavelength bands separated by the dispersive elements 28, 28' are directed towards the pluralities of waveguides 29, 29', respectively, such that each separate wavelength band will be collected by a different one of the waveguides in the pluralities 29, 29' as a separate wavefront. Preferably the wavelength crosstalk between adjacent waveguides in the pluralities 29, 29' will be better than –20 dB and more preferably better than –30 dB, as shown in FIG. 6. Although the wavelength spectrum shown in FIG. 6 shows equally spaced wavelength bands, equal spacing of the bands is not required, and this can be adjusted, according to the fluorescent markers used. Furthermore the wavelength or wavelength bands $\lambda_1, \ldots, \lambda_m$, and $\lambda_1, \ldots, \lambda_n$ may interleave as shown, or the may be arranged in a different way with respect to one another.

Light transmitted through the output waveguides 29, 29' of the light directing means 19 is passed on to the detection means comprising two groups of detectors 31, 31', respectively, each having a plurality of detectors; each group of detectors 31, 31' being mounted on planar detector substrate devices 30, 30', respectively. The substrate devices 30 and 30' may be butt-coupled to the edge of the substrate 80 as described in more detail in FIG. 3a.

FIG. 3a shows a detailed view of the interface of the plurality of output waveguides 29 with the detector substrate 30. The detector substrate 30 and the side face of the substrate 80 in the region where the waveguides 29 extend to the edge of the substrate 80 are polished, respectively, and butt-coupled. The substrate 30 may be attached to the substrate 80 by means of transparent glue or resin. The detectors 31 may be top-entry photodiodes that are flip-chip bonded over etched v-grooves in the detector substrate 30, that extend from the edge of the substrate 30 that is coupled to the edge of the substrate 80 to a location underneath the entry face of each photodiode. For this purpose the detector substrate 30 may conveniently be made of crystalline silicon which can be etched to form v-grooves 35 with a selective crystallographic etch, such as described in U.S. Pat. No. 4,945,400. By using this processing method the v-groove formed in this manner will automatically terminate in an inclined end face that can be used to reflect light upwards into the entry face of the photodetector. U.S. Pat. No. 4,945,400 also describes a way of coating the end face with a metal layer 32 which extends over the end of the v-groove 35 and simultaneously serves to enhance the reflectivity of the end face of the groove and provides for a soldering pad and top contact for the photodetectors 31. With this arrangement in place signal leads 33, 34 can conveniently be attached to the metal layer 32 and the bottom contact of the photodiode 31 which lead to an electronic processing circuitry 100.

In an alternative embodiment of the present invention (not shown), the pluralities of detectors 31 and 31' may be hybridised directly on the same substrate device 80 that comprises the pluralities of output waveguides 29, 29', respectively. This can be carried out by using the detector hybridisation technology described in WO9835253 or using other techniques well known in the art of integrated optics. For example, if a silica or silica on silicon substrate is used for providing the waveguides, a rectangular recess can be etched into the substrate and a top entry photodiode may be glued down sideways into the recess, abutting the relevant waveguide with its top entry facet. Connections to the photodiode can then be made by soldering directly to the top and bottom facets of the diode on the portion of the diode protruding from the substrate 80.

Figure 2B:
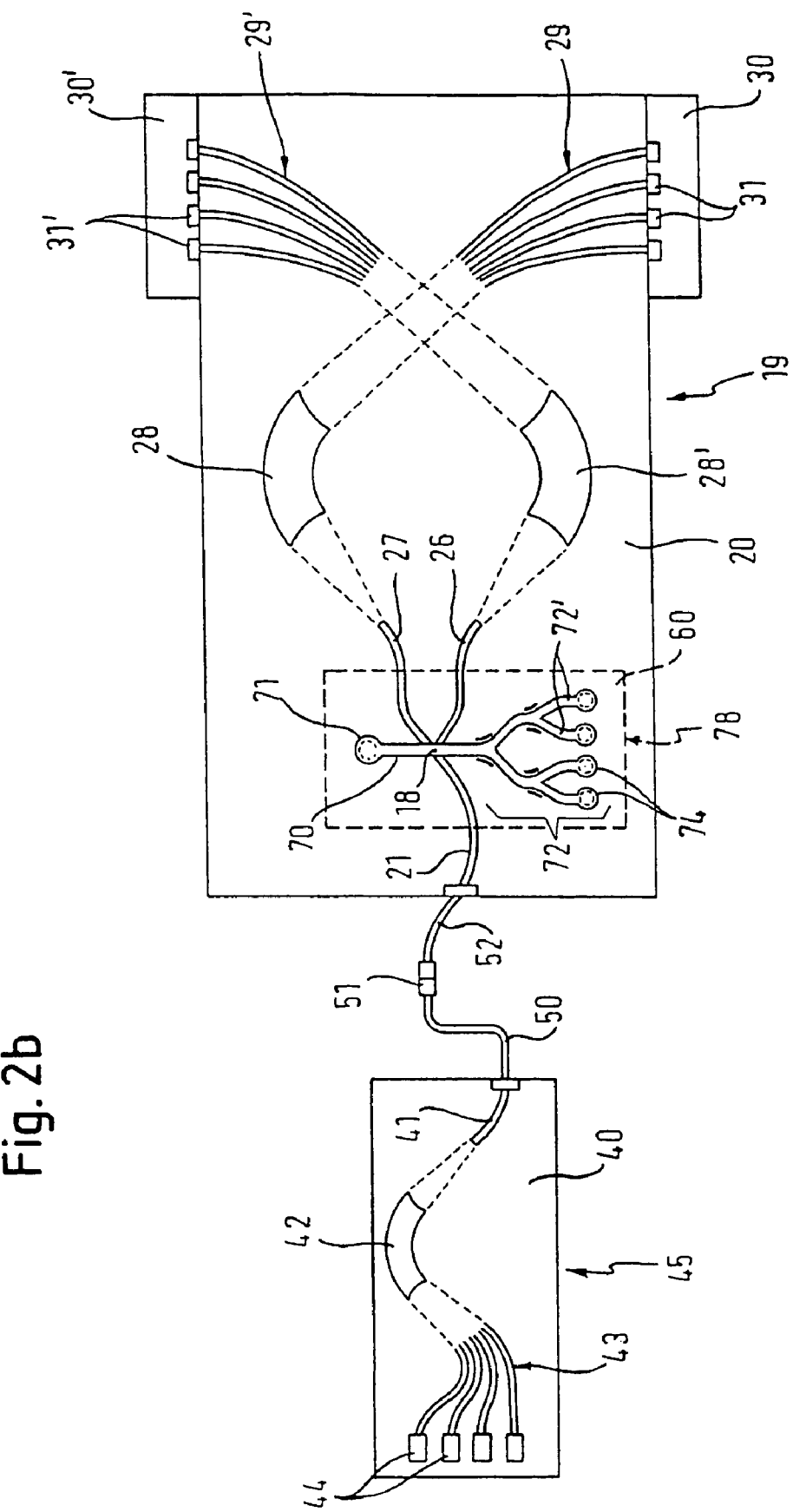
FIG. 2b is a schematic top view of an optical detection device according to another embodiment of the present invention.

Another preferred embodiment of the present invention is shown in FIG. 2b. Here, the analyte handling means analyte means 78 is integrated on the same substrate 20 as the light directing means 19 of the optical detection device, which comprises the dispersive elements 28, 28', the plurality of output waveguides 29, 29'. The detector substrates 30, 30' carrying the pluralities of detectors 31, 31' are coupled to the substrate 20 in the same way as described before for substrate 80 in FIG. 2a. In this case a separate fibre optic connection between the analyte means 78 and the light directing means 19 is not necessary.

In yet another embodiment of the invention (not shown) the light supplying means 45 may be integrated on the same substrate 20 as well. Whether all or some of the light supplying means, the analyte handling means and the light directing and detection means will be integrated on the same substrate or be provided on separate substrates which are connected by optical fibres will depend on the final manufacturing processes chosen, the expected manufacturing yields of the final devices and the specific applications envisaged.

If integration of the light supplying means, the analyte handling means and the light directing and detection means on separate substrates is chosen, this will allow these components to be exchanged or maintained separately, should one of them fail in operation. Further, such an embodiment would have the advantage that these devices can be physically separated by an appreciable distance. In such a situation the low loss of optical communication fibres will allow the separation of the light supplying means, the analyte handling means and the light directing means by several meters, or even several tens of meters. This would have the advantage that the analyte handling means can for example be located in a higher containment level compartment than the light supplying means and the light detecting means, or that these devices can be distributed over different locations in the same building.

Figure 3B:
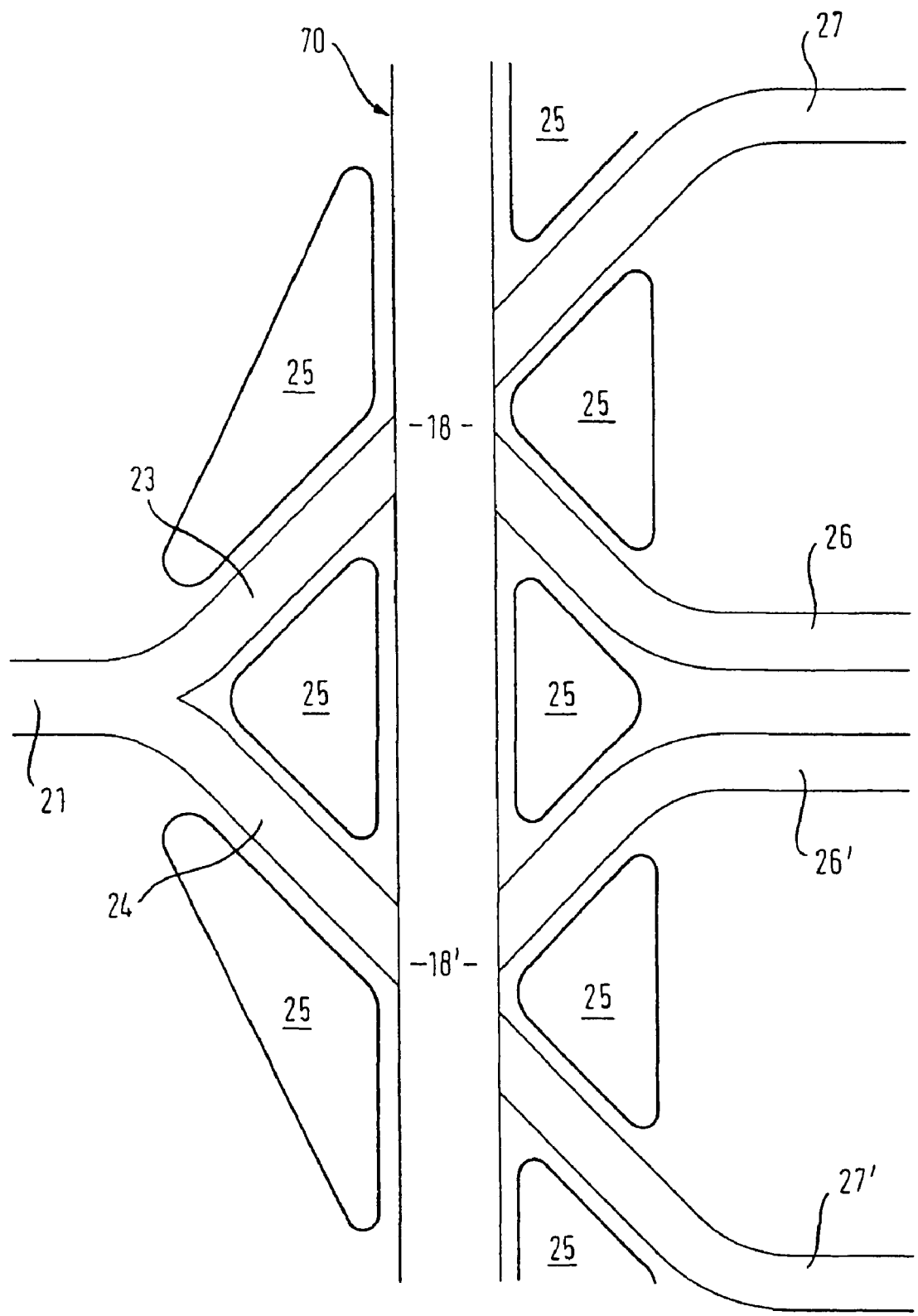
FIG. 3b is a schematic enlarged top view of an alternative embodiment of the waveguide interfaces with the analyte channel in the optical detection device.

In a preferred embodiment shown in FIG. 3b the waveguide 21 splits via a y-junction into waveguides 23 and 24, which both interface with the analyte channel 70 at an angle such that light refracted across the boundary of the waveguide with the analyte channel enters the liquid suspension or solution guided in the channel at an angle of between 30 and 60 degrees and more preferably at an angle of 45 degrees within two different interrogation regions 18' and 18". On the opposite side of the analyte channel 70 waveguide 27 collects forward scattered light and waveguide 26 collect side scattered and fluorescent light emitted from the interrogation region 18' and the waveguide 27' collects forward scattered light and waveguide 26' collects side scattered and fluorescent light emitted from the interrogation region 18", respectively. The choice of the interface angles of the various waveguides and the general design of these interfaces follow the same principles as those described in the previous example of FIG. 2a. The advantage of such an arrangement is that a measurement of the analyte content is taken at two successive interrogation points 18' and 18" which allows for a direct determination of the flow speed and dynamics of the analytes propagating in the analyte channel 70. This may have the advantage of allowing more accurate sorting of analytes if such were required and detecting any differential motion in the analytes In FIG. 3b there are also shown absorbing regions 25 to lower the noise level of scattered, unguided light travelling around the substrate 20. A plurality of such doped absorbing regions 25 are included on the substrate 20 in the vicinity of the waveguides 23, 24, 26, 27 and their interfaces with the analyte channel 70. Such absorbing regions are for example described in WO 9928772.

A detailed view of the analyte handling means 78 comprising an analyte sorting means 72 is shown in FIG. 3c. The analyte sorting region 72 is formed as a cascade of y-junctions branching the analyte channel 70 into $2^N$ sorting channels (N being the number of stages in the cascade) in a plurality 72' that terminate in a plurality of $2^N$ output ports 74. The number of terminal sorting channels 72' is preferably greater or equal to the number of fluorescent wavelengths used for detecting the properties of the analytes. As described above, the sorting channels in the plurality 72' as well as the analyte channel and their y-junctions are formed as trenches etched into the substrate 20, e.g. by means of a reactive ion etch process, and the ports 70 and 74 are formed as extended recesses in the substrate 20 by means of a similar etch process.

Figure 4:
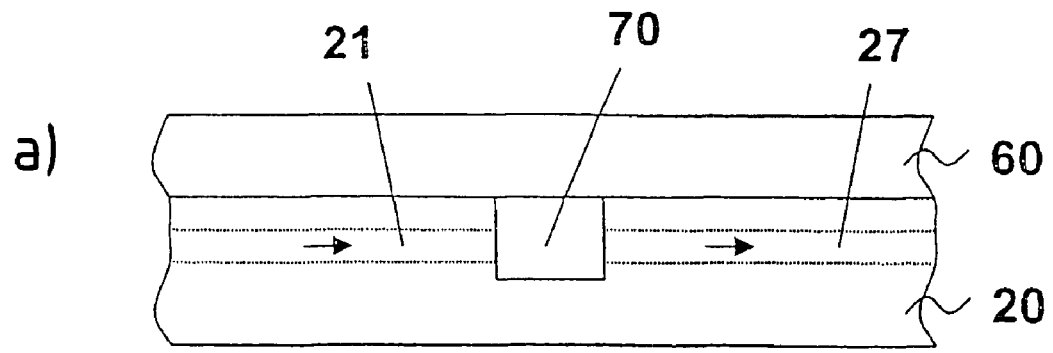
FIG. 4a is a cross section along line A-A in FIG. 3c, showing the analyte channel and buried waveguides in the optical detection device.
FIG. 4b is a cross section along line B-B in FIG. 3c, showing the analyte channel and buried sorting elements.
FIG. 4c is a cross section along line C-C in FIG. 3c, showing the analyte input of the analyte handling means of the present invention.
Figure 4:
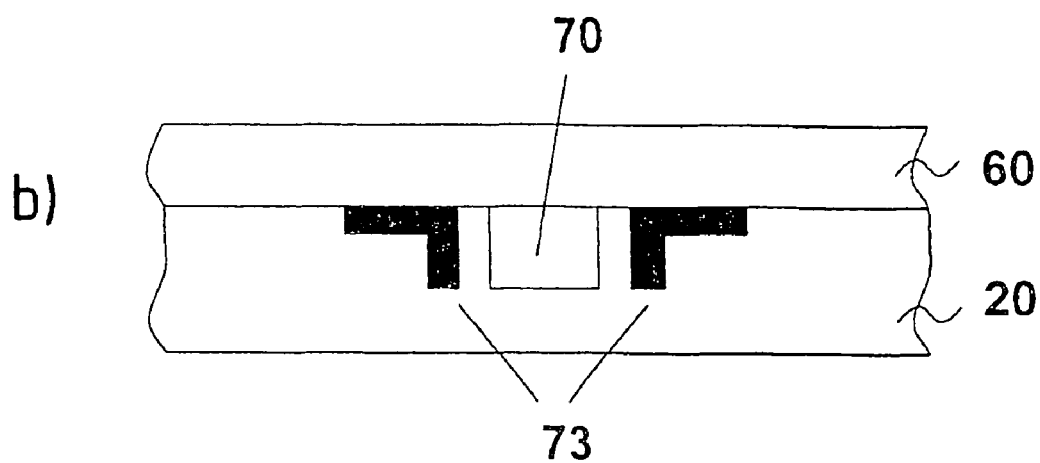
Figure 4:
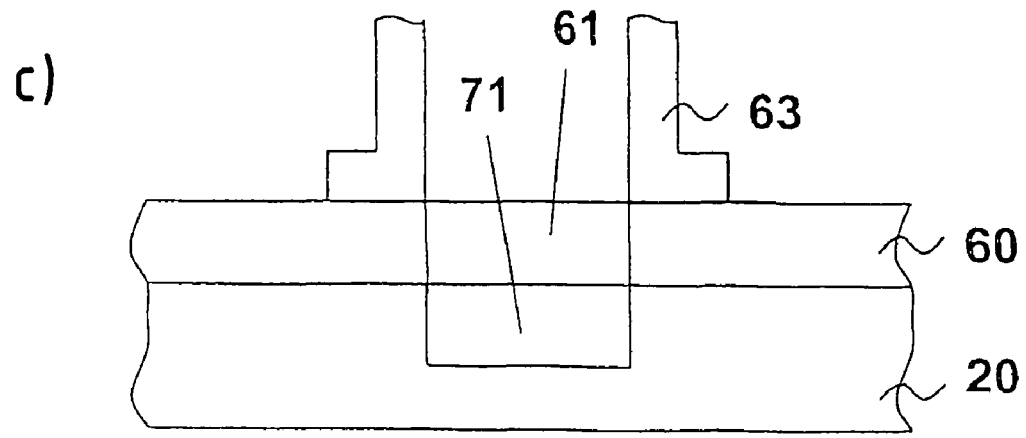

Each analyte channel y-junction in the analyte sorting means 72 contains a pair of sorting elements 73. In the preferred embodiment shown, the sorting elements 73 are opposite polarity electrodes that are buried on either side of the analyte channels in the sorting means 72 adjacent to each y-junction as extended recesses. FIG. 4b shows a cross section of the analyte channel 70 and the electrodes 73 along the line B-B of FIG. 3c. The electrodes 73 extend on either side of the etched analyte channel into the substrate device 20 from the top of the substrate. This can be achieved by etching the substrate on either side of the analyte channel with a directional etch process, such as a reactive ion etch and subsequently depositing a metal layer through a mask into the etched recesses. As shown in the Figure, the top surface area of each electrode 73 is enlarged to allow for convenient connection of electrical lead traces 75 (shown in FIG. 3c) extending over the top of the substrate 20. The electrodes 73 may be in direct contact with the analyte channel 70 or they may be separated from the channel by dielectric walls in the substrate, as shown in FIG. 4b. As is shown in detail in FIG. 3c, on the surface of the substrate device 20 a plurality contact traces 75 is formed by lithographic processes that extends from the electrodes 73 to the edge of the substrate 20 allowing for an electronic control unit 76 to be connected to the contact traces 75 via a plurality of external leads 77 for controlling the electrodes 73 in FIG. 3c.

When the detection section is used for analyte sorting the analytes used are either negatively or positively charged. This can be achieved, for example, by coating all analytes with microbeads via a common surface marker, whereby the beads will carry a negative or positive ionic charge in suspension or solution, e.g. due to a coating of the beads with Ni Fe or Cu ions. Analytes that pass the interrogation region 18 are illuminated by light emitted at the light supplying means and transmitted by the waveguide 21. The light emerging from the interrogation region 18 is collected by the waveguides 26, 27 and is guided to the detectors 31. If the width of the analyte channel, the flow rate of the analytes and the concentration of the analytes are all such that only one particle to be analysed passes the waveguide 21 at a time, the speed of the analytes in the channel can be accurately predicted. Taking into account the hydrodynamic properties of the sorting region 72 an accurate determination can be made as to when the analyte particle passes each y-junction and as appropriate each in the plurality of pairs of electrodes 73 can be used to redirect each analyte particle into a y-junction branch according to the fluorescent wavelength detected. In such a case, the electric field applied to each in the plurality of pairs of electrodes 73 should be strong enough to redirect the flow of a particle, but not so strong that the particle gets immobilised against the wall of the analyte channel.

Figure 2C:
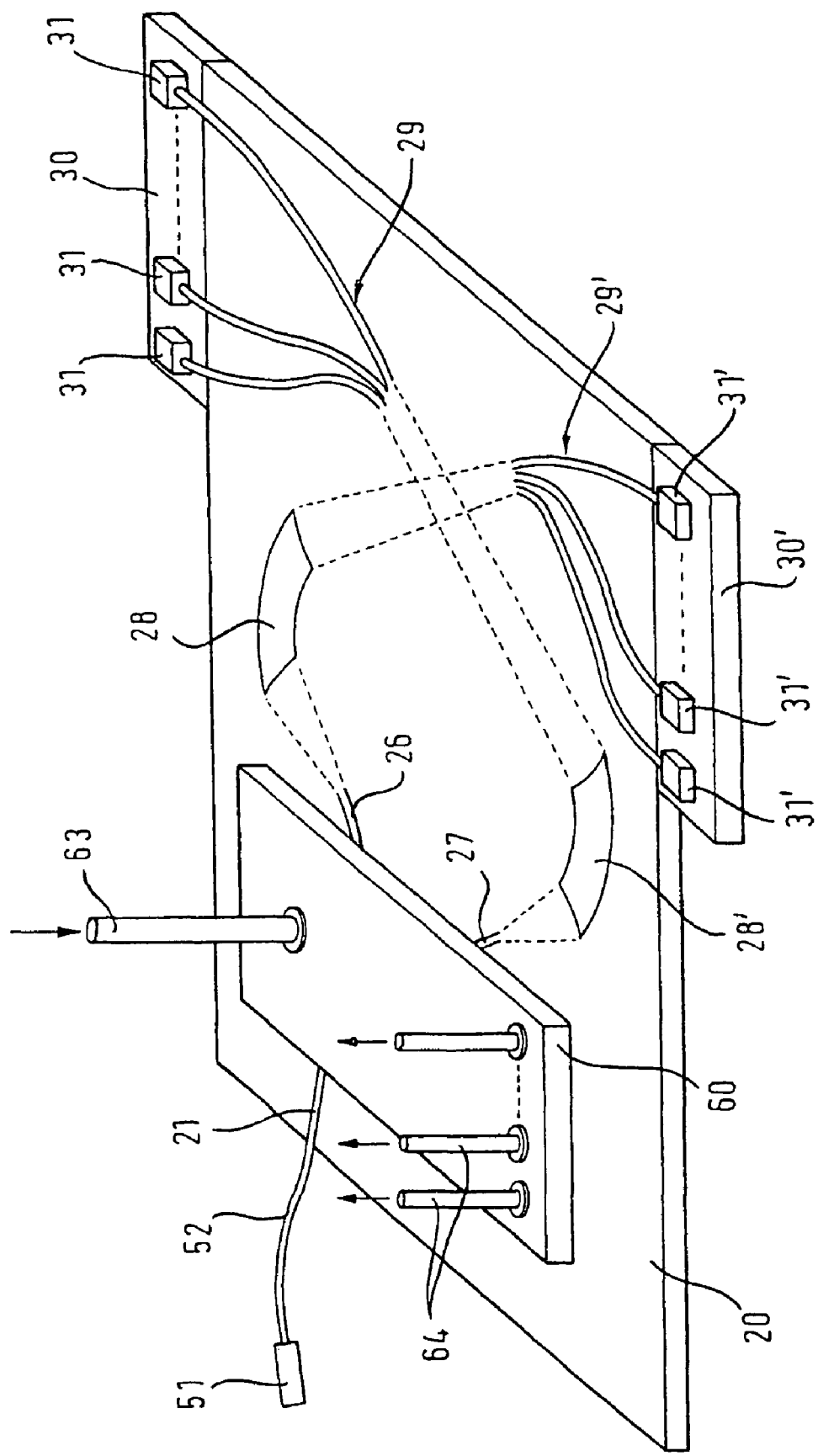
FIG. 2c is a schematic perspective view of a part of the optical detection device of FIG. 2b showing a substrate covering an area within the analyte handling means.

As described above the analyte channel 70 and the analyte sorting channels 72' are formed as extended recesses in the substrate device 20, which means they are open towards the top surface of the substrate device 20. To seal the channels a substrate 60 extending over the area around the analyte channel 70 and the analyte sorting channels 72' is bonded to the top surface of substrate 20. The horizontal boundary of the substrate 60 corresponds to the dashed lines in FIG. 2b. The substrate presence 60 is shown in more detail in FIG. 2c. At the location of the analyte input port 71 and of each of the plurality of output ports 74 apertures 61, 62 are formed in the sealing substrate 60 such that liquid guiding means 63, 64 can be connected to each port. A cross section of the interface between the liquid guiding means 63 with the aperture 61 in the region of the input port 71 is shown in further details in FIG. 4a. Bonding of the substrate device 60 to the substrate device 20 may be achieved simply by polishing both bond surfaces and creating a contact bond which is maintained by the van der Waals interactions between the substrates 20 and 60. To be able to polish the surface of the substrate 20, either a buried waveguide structure will have to be used, or, when if silicon-on-insulator ridge waveguides are used, an additional amorphous silica or other layer may have to be deposited on top of the waveguide structures and be polished back to a smooth surface before the bonding is carried out. Other means of bonding include glues or resins, or soldering, according to methods well known in the art, but it is important that no such glues, resins or solders interfere with the optical properties of the optical waveguides or the analyte channel on the substrate.

A cross-section of the connection between the substrate device 20 and the substrate 60 in the region of the analyte input port 71 is shown in FIG. 4c. Substrate 20 comprises a recess for the liquid input port 71. The aperture 61 in the substrate 60 is located exactly above the port 71. On the top surface of substrate 60 there is positioned the liquid input guiding means 63, which has a flanged connection with the substrate 60. The liquid output guiding means 64 are arranged in the same manner above the output ports 74.

In one embodiment the analyte flow is injected into the input port 71 through the liquid guiding means 63, preferably at a predetermined, constant flow rate. The analyte flow is directed through the analyte channel 70 via the sorting means 72 to the output ports 74 where it is received by the liquid output guiding means 64. If it is an objective to reduce the possibility of clogging of the analyte channel 70 with aggregated analytes in suspension, such as clumps of cells, an appropriate pre filter can be used.

Figure 5A:
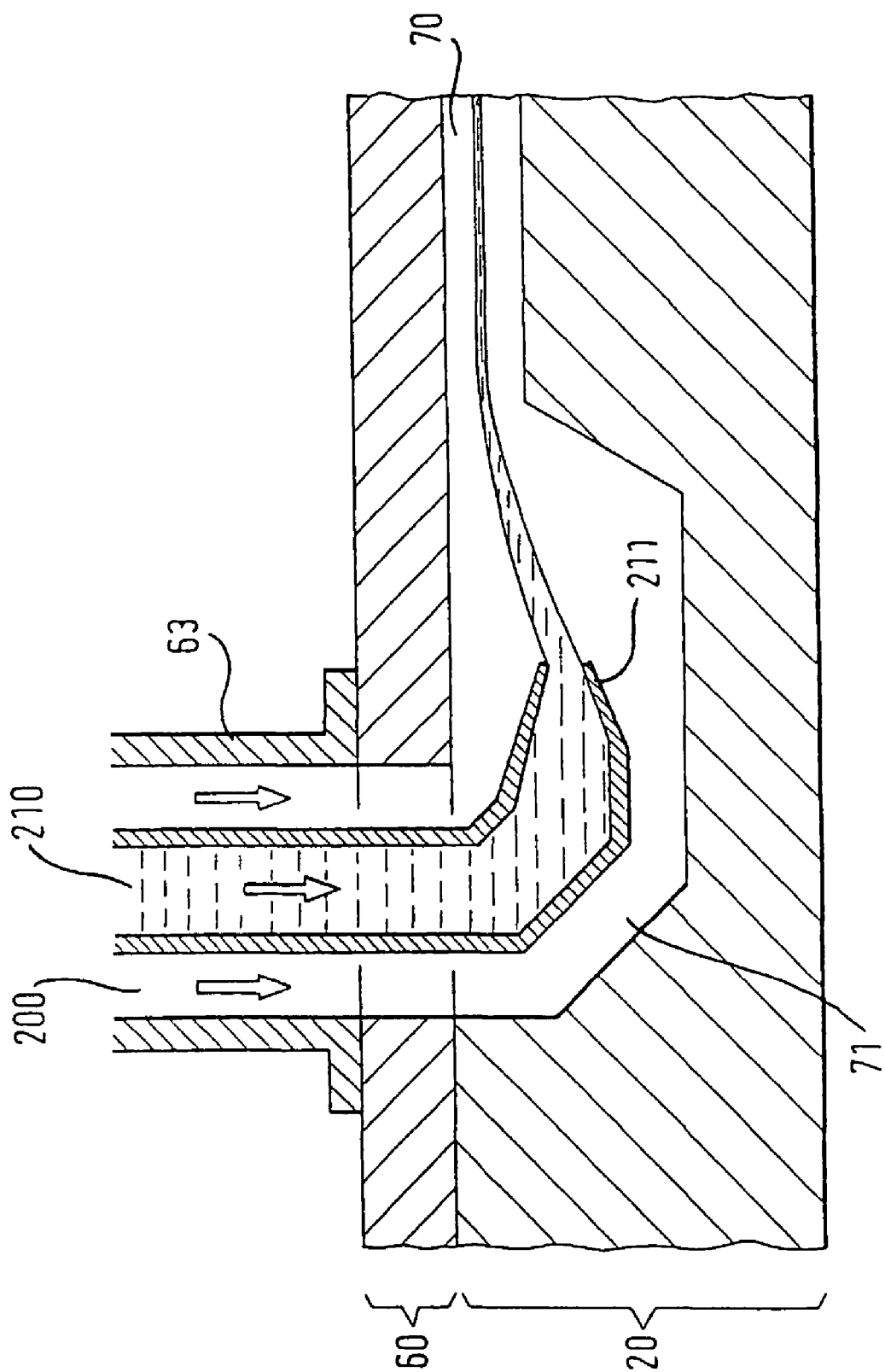
FIG. 5a is a cross section view, showing the analyte input region comprising an additional system for hydrodynamic focussing.

In still another embodiment of the analyte handling means according to FIG. 5a, there is provided a first liquid guiding means in the form of an input channel 200 for introducing a sheath fluid into the analyte channel and a second liquid guiding means in the form of a second input channel 210 for introducing the analyte suspension or solution. The channel 210 is concentric with the channel 200 in the region above the substrate 60. Following the direction of the analyte flow the channel 200 then interfaces with the substrate 60, whereas the channel 210 extends into the cavity of the input port 71, which is over-etched vertically to accommodate this additional device. The channel 210 then curves by 90 degrees towards the analyte channel 70 and ends with a conical nozzle 211 pointing towards the channel 70 for introducing the analyte suspension or solution into the analyte channel 70. The sheath fluid is introduced in the first input channel 200 with a velocity that is at least equal to or higher than the velocity of the analyte suspension or solution, emerging from the nozzle 211, such that when the analyte liquid suspension or solution is introduced out of the nozzle 211 into the surrounding flow of sheath fluid, both the analyte flow and the flow of the sheath fluid will converge into the analyte channel 70 and the analyte flow will be focused into the centre of the cross section of the analyte channel 70 according to the Bernoulli-Effect of hydrodynamic focusing that was described previously. As a result the analytes are confined in the centre region of the analyte channel, forming an analyte flow in the centre of a parabolic pressure distribution along the cross-section of the analyte channel 70.

As is usual in flow cytometry applications, both the sheath fluid and the buffer fluid for the analyte suspension or solution will be phosphate buffered saline or a similar electrolyte solution.

Figure 5B:
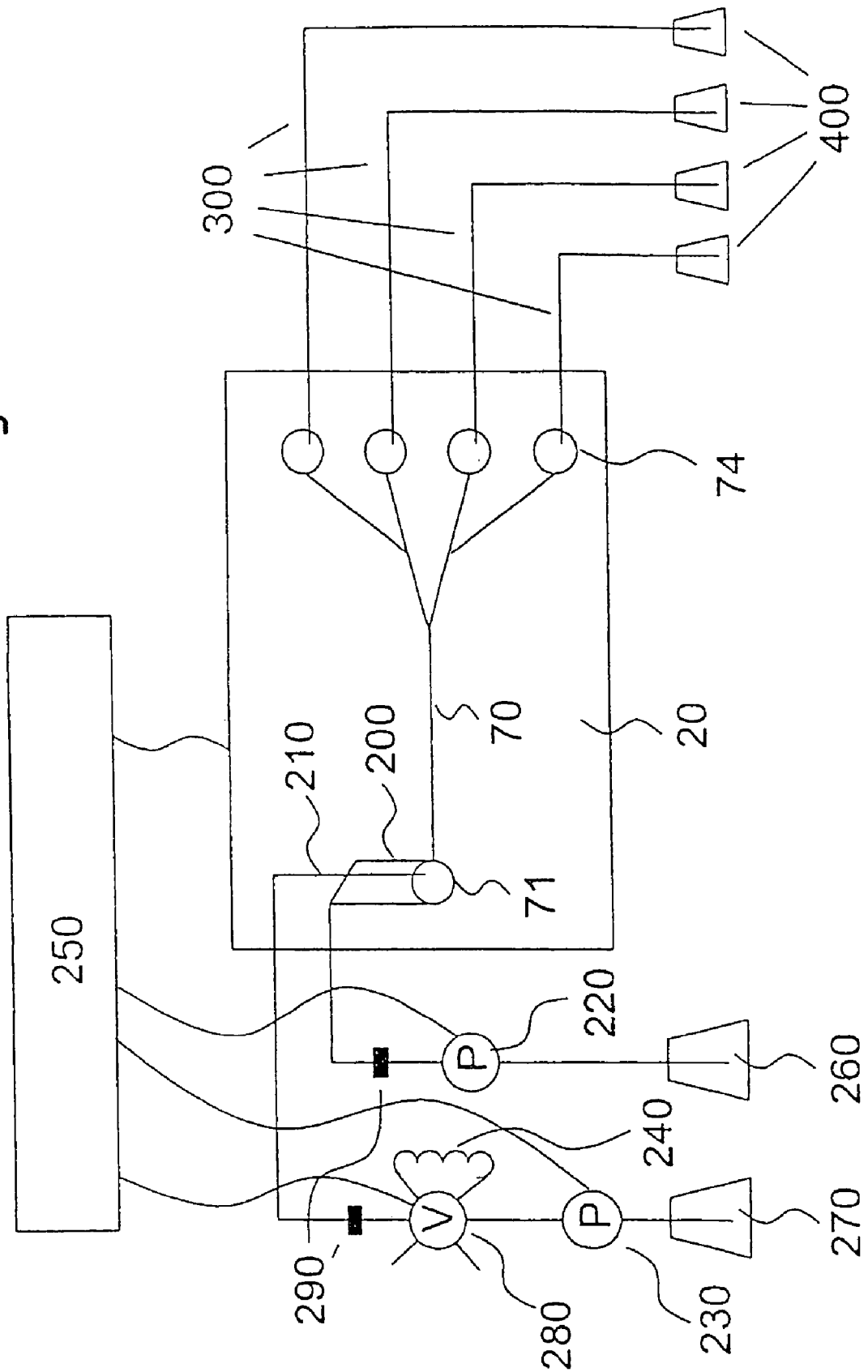
FIG. 5b is a schematic view of the external fluid handling arrangement of an analyte handling means.

FIG. 5b illustrates an arrangement for providing the sheath fluid and the liquid suspension or solution, for use with the hydrodynamic focusing assembly shown in FIG. 5a. For simplicity, the waveguides are not shown on the substrate 20 in this figure. The sheath fluid is pumped by a pump 220 from the reservoir 260 through the one of pre-filters 290 and channel 200 to the input 71 of the analyte channel analyte channel 70. A second pump 230 will pump suspension or solution buffer from the reservoir 270 to the analyte injection valve 280. The pumps 220 and 230 may be similar to those commonly used in protein liquid chromatography and the injection valve 280 may be an injection valve commonly used in liquid chromatography applications. An injection loop 240 is then used in conjunction with the valve 280 to bring a sample of analyte suspension or solution in line with the analyte sample buffer flow emerging from pump 230 which is conducted via the channel 210 through the other of prefilters 290 to the input 71. The pumps 220, 230 and the injection loop 240 are controlled electronically by a controller 250.

In case of an embodiment of the analyte handling means 78 according to FIG. 3a, in which two incident waveguides 23, 24 are and four emergent waveguides 26, 26', 27, 27' are used, twice the number of dispersive elements in the light directing means 19 and groups of detectors 31 in the detection means may be used to detect the signals collected by the waveguides 26, 26', 27, 27'.

In still an other embodiment of the present invention any or all elements, i.e. the light supplying means, the analyte sorting and interrogation region 18 and the signal detection region may be temperature controlled in order to ensure a uniform and repeatable operating environment. Due to the substrate integration of both the optical and fluidic components of the system this can be achieved conveniently by mounting the respective substrates on Peltier cooling devices. Such devices are available commercially and they will allow for a compact design of a cooled packaged device.

The present invention in its broader aspects is not limited to the specific details illustrated in the foregoing examples and shown in the figures. Various modifications may be made without departing from the spirit of the invention.

If, for example, only fluorescent detection is required and not analyte sorting, it may favourable that the analyte channel 70 be unbranched, i.e. it would not contain an analyte sorting region 72 and the device would only have a single analyte-output port 74.

In another embodiment the analyte channel 70 of the analyte handling means extends along an edge of the substrate device 20 such that light illuminating the analytes in the interrogation region 18 in the analyte channel can be received directly from the edge of the substrate.

As mentioned before, in certain embodiments of the invention the number of fluorescent wavelengths may be larger than the number of incident wavelengths, i.e. some or all of the fluorescers may share a common wavelength for their absorption maximum while each having a different wavelength for their emission maximum. Such a method is commonly used in prior art devices, as this will reduce the complexity of the light supplying means. On the other hand restricting the number of excitation wavelengths may reduce the number of appropriate fluorescers available, as it may not be possible to find a sufficiently large number of fluorescers for any given application that share a common excitation maximum while having different fluorescent emission maxima. In any event a device constructed according to the present invention, as described above, will provide substantially improved design flexibility in finding the ideal trade-off between the number of excitation wavelengths used and the fluorescent dyes or particles chosen for any given application.

In another embodiment of the invention light incident on the interrogation region 18 may be introduced to interrogation region 18 by directing it along the analyte channel 70 instead of guiding it along a waveguide 21 through the substrate 20, i.e. the analyte channel itself is used as a light waveguide. In this case the incident light is guided parallel to the liquid flow into the interrogation region 18.

The invention claimed is:

1. Device for analysing analytes in a liquid suspension or solution comprising:

analyte handling means including an analyte input region and an analyte channel for carrying analytes in a liquid suspension or solution through an interrogation region to an analyte output region; and light guiding means for directing light emerging from the analytes in the interrogation region to optical detection means for detecting one or more properties of the analytes in the suspension or solution, wherein the light guiding means comprises, a first output optical waveguide to receive scattered light emerging from the interrogation region, a dispersive element to receive said scattered light from the first output optical waveguide, and at least one waveguide for collecting light from the dispersive element;

wherein at least the analyte channel and the output optical waveguide are integrated on a first planar substrate and the dispersive element is integrated on a second planar substrate.

2. Device as claim in claim 1, wherein the first and second planar substrates are the same planar substrate.

3. Device as claimed in claim 1, wherein at least one dispersive element, at least one optical waveguide for carrying light towards each dispersive element, and a plurality of output waveguides for collecting light of wavelengths or wavelength bands $\lambda_1 \ldots \lambda_m, \lambda'_1 \ldots \lambda'_n$ output from each dispersive element are integrated on the second planar substrate.

4. Device as claimed in claim 3, wherein the dispersive element is an arrayed waveguide grating or a transmission grating integrated on the second planar substrate.

5. Device as claimed in claim 1, wherein one dispersive element, an optical waveguide for carrying light towards the dispersive element, and a plurality of output waveguides for collecting light of wavelengths or wavelength bands $\lambda_1 \ldots \lambda_m$, $\lambda'_1, \ldots \lambda'_n$ output from the dispersive element are provided (1) for separating forward scattered light received from the first output optical waveguide and (2) for separating side scattered light received from a second output optical waveguide.

6. Device as claimed in claim 1, wherein the light guiding means comprises at least one optical detector integrated in or hybridised on a third planar substrate.

7. Device as claimed in claim 6, wherein a plurality of optical detectors are provided on the third planar substrate with one optical detector being provided for detecting each of a plurality of wavelengths $\lambda_1 \ldots \lambda_m, \lambda'_1 \ldots A'_n$.

8. Device as claimed in claim 7, wherein one or more of the optical detectors are photodiodes, and wherein each optical detector is mounted over an inclined end face at the end of a v-groove formed in the third substrate, the v-groove extending to the edge of the substrate.

9. Device as claimed in claim 1, comprising analyte sorting means for sorting analytes in a liquid suspension or solution received from the analyte output region, comprising a plurality of sorting channels comprising at least one y-junction integrated on the first planar substrate, wherein a pair of opposite polarity electrodes are formed in the first planar substrate on either side each of said y-junctions.

10. Device as claimed in claim 1, further comprising:
light supplying means having a first input optical waveguide for directing light into the interrogation region, the light guiding means comprises,
the first output optical waveguide positioned to receive forward scattered light emerging from the interrogation region,
a second output optical waveguide positioned to receive side scattered light emerging from the interrogation region at an angle to forward scattered light,
the second output optical waveguides also being integrated on the first planar substrate.

11. Device as claimed in claim 1, further comprising:
light supplying means having a first input optical waveguide for directing light into the interrogation region and a second input waveguide for directing light into a second interrogation region in the analyte channel spaced from the interrogation region, the light guiding means comprises,
the first output optical waveguide positioned to receive forward scattered light emerging from the interrogation region,
a second output optical waveguide positioned to receive side scattered light emerging from the interrogation region at an angle to forward scattered light,
a third output optical waveguide positioned to receive forward scattered light from the second interrogation region, and
a fourth output optical waveguide positioned to receive side scattered light emerging from the second interrogation region at an angle to the forward scattered light, the third and fourth output optical waveguides also being integrated on the first planar substrate.

12. Device as claimed in claim 11, wherein the first input waveguide and the analyte channel are formed by the same recess in the first substrate, such that incident light is introduced into the interrogation region by directing light along the analyte channel.

13. Device as claimed in claim 1, comprising light supplying means having a light source for emitting light with a predetermined characteristic, which is changeable by interaction of the light with the analytes in the suspension or solution according to the properties of the analytes.

14. Device as claimed in claim 1, wherein the light supplying means comprises a light source for emitting light of one or more discrete wavelengths or wavelength bands $\lambda, \lambda_1 \ldots \lambda_m$, and wherein the one or more wavelengths or wavelength bands $\lambda, \lambda_1 \ldots \lambda_m$ is selected according to the properties of the analytes to be investigated.

15. Device as claimed in claim 1, wherein the optical detection means can discriminate one or more wavelengths or wavelength bands $\lambda, \lambda_1 \ldots \lambda_m$ and one or more wavelength or wavelength bands $\lambda'_1 \ldots \lambda'_n$ emitted by the analytes as a consequence of fluorescence.

16. Device as claimed in claim 1, wherein first liquid guiding means is provided for introducing sheath fluid into the analyte channel and second liquid guiding means is provided for introducing the analyte suspension into the analyte channel, wherein the first and second liquid guiding means are formed such that they allow for hydrodynamic focusing of the anlayte suspension or solution into the centre of the analyte channel.

17. Device as claimed in claim 1, wherein the light supplying means comprises one or more components integrated on a fourth planar substrate optically connected to the first planar substrate, wherein one or more light emitting diodes or laser diodes are provided on the fourth planar substrate, and wherein at least one integrated optical waveguide for carrying light from each of the light emitting diodes or laser diodes is provided on the fourth planar substrate.

18. Device as claimed in claim 17, wherein a dispersive element is integrated on the fourth planar substrate for combining light of different wavelengths $\lambda_1 \ldots \lambda_m$, received from a plurality of waveguides into a single waveguide.

19. Method for investigating the properties of one or more analytes in a liquid suspension or solution, comprising:
carrying analytes in a liquid suspension or solution through a light receiving region in an analyte channel on a first substrate;
supplying light to the light receiving region to illuminate an interrogation region of the analyte channel;
directing light emerging from the analytes in the interrogation region to at least one optical detector configured to detect one or more properties of the analytes in the suspension or solution, wherein said directing light comprises,
receiving scattered light emerging from the interrogation region in a first output optical waveguide in the first substrate, and
receiving said scattered light in a dispersive element in a second substrate,
collecting light from the dispersive element in at least one output optical waveguide; and
outputting data representative of said dispersed received scattered light to a receiving device or a user.

20. Method as claim in claim 19, wherein the first and second substrates are the same substrate.

* * * * *